United States Patent [19]

Nelson et al.

[11] Patent Number: 5,922,715
[45] Date of Patent: Jul. 13, 1999

[54] 5-AMINOALKOXY-1, 4-DIHYDROQUINOXALINE-2, 3-DIONES

[75] Inventors: James Albert Nelson, Washington Crossing, Pa.; Uresh Shantilal Shah, Cranbury; Richard Eric Mewshaw, Princeton, both of N.J.

[73] Assignee: American Home Products Corporation, Madison, N.J.

[21] Appl. No.: 09/025,018

[22] Filed: Feb. 17, 1998

Related U.S. Application Data

[60] Provisional application No. 60/038,683, Feb. 18, 1997.
[51] Int. Cl.$^6$ ............... A61K 31/495; C07D 241/44
[52] U.S. Cl. .................................. 514/249; 544/354
[58] Field of Search ............... 544/354; 514/249

[56] References Cited

U.S. PATENT DOCUMENTS 4,140,789  2/1979  Jaeggi ........................ 424/248.55

FOREIGN PATENT DOCUMENTS

| | | |
|---|---|---|
| 0315959 | 5/1989 | European Pat. Off. . |
| 0377112 | 11/1990 | European Pat. Off. . |
| 0707007 | 4/1996 | European Pat. Off. . |
| WO9015606 | 12/1990 | WIPO . |
| WO9211012 | 7/1992 | WIPO . |
| WO9212134 | 7/1992 | WIPO . |
| WO9400124 | 1/1994 | WIPO . |
| WO9609295 | 3/1996 | WIPO . |
| 96/37500 | 11/1996 | WIPO . |
| WO9723216 | 7/1997 | WIPO . |

OTHER PUBLICATIONS

Huth et al, Chemical Abstracts, vol. 126, No. 75066,(Abstract for DE 19,519,979), 1997.
Van Tol, Nature, vol. 350, pp. 610–614, 1991.
Jaen J.C. et al., Journal of Med. Chem., vol. 31, No. 8 (Aug. 1988) pp. 1621–1625.
Benes, F.M., Biol. Psychiatry, vol. 38 (1995) pp. 783–787.
Olney, J.W. et al., Arch. Gen. Psychiatry, vol. 52 (1995) pp. 998–1007.
Starr, M.S. et al., Eur. J. Pharmacol., vol. 250 (1993) pp. 239–246.

*Primary Examiner*—Emily Bernhardt
*Attorney, Agent, or Firm*—Robert F. Boswell, Jr.; Arthur G. Seifert

[57] ABSTRACT

This invention relates to compounds of Formula I

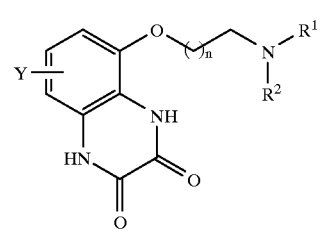

wherein:
  $R^1$ and $R^2$ are independently selected from hydrogen, straight-chain and branched alkyl group having up to 10 carbon atoms or —$(CH_2)_m$Ar where Ar is phenyl, naphthyl or thienyl, each optionally substituted by one or two substituents selected independently from $C_1$–$C_6$ alkyl, halogen, $C_1$–$C_6$ alkoxide and trifluoromethyl;
  or $NR^1R^2$ is 1, 2, 3, 4-tetrahydroquinolin-1-yl or 1, 2, 3, 4-tetrahydroisoquinoline-2-yl;
  m is 1–5;
  n is 1 or 2;
  Y is hydrogen, $C_1$–$C_6$ alkyl, and $C_1$–$C_6$ alkoxy;
or the pharmaceutically acceptable salts thereof, which are dopamine $D_2$ agonists and therefore useful in the treatment of psychoses and Parkinson's disease.

7 Claims, No Drawings

5-AMINOALKOXY-1, 4-DIHYDROQUINOXALINE-2, 3-DIONES

This application claims benefit of priority to provisional patent application 60/038,683 filed Feb. 18, 1997.

FIELD OF THE INVENTION

This invention relates to N-substituted 5-aminoethoxy-1, 4-dihydroquinoxaline-2,3-diones which are dopamine $D_2$ agonists and therefore useful as antipsychotic agents and anti-parkinson agents.

BACKGROUND OF INVENTION

Efforts to induce antipsychotic activity with dopamine autoreceptor agonists have been successful (Dorsini et al. *Adv. Biochem. Psychopharmacol.*, 16, 645–648, 1977; Tamninga et al., *Science*, 200, 567–568, 1975; and Tamminga et al., *Psychiatry*, 398–402, 1986). A method for determining intrinsic activity at the dopamine $D_2$ receptor was recently reported (Lahti et al. *Mol. Pharm.*, 42, 432–438, 1993) Intrinsic activity is predicted using the ratio of the "low-affinity agonist" (LowAg) state of the receptor and the "high-affinity agonist" (HighAg) state of the receptor, i.e. LowAg/HighAg. These ratios correlate with the agonist, partial agonist, and antagonist activities of a given compound, which activities characterize a compounds ability to elicit an antipsychotic effect. The compounds of this invention are dopamine agonists various degrees of intrinsic activity some of which are selective autoreceptor agonists, and therefore partial agonist (i.e. activate only autoreceptors versus postsynaptic $D_2$ dopamine receptors). As such, they provide functional modulation of the dopamine systems of the brain without the excessive blockade of the postsynaptic dopamine receptors which have been observed to be responsible for the serious side effects frequently exhibited by agents found otherwise clinically effective for the treatment of schizophrenia. Activation of the dopamine autoreceptors results in reduced neuronal firing a well as inhibition of dopamine synthesis and release and therefore provide a means of controlling hyperactivity of the dopaminergic systems. The compounds of this invention were also found to have high intrinsic activity and therefore they can behave as the natural neurotransmitter i.e. as full agonists. As such, they are useful in the tent of diseases having abnormal concentrations of dopamine could be used as dopamine surrogates possibly in the treatment of Parkinson's disease.

The compounds of this invention are essentially free of extrapyramidal side effects.

SUMMARY OF THE INVENTION

The compounds of this invention are represented by the following Formula I:

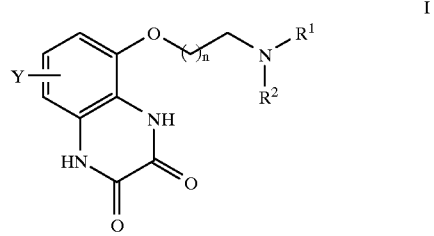

wherein:
$R^1$ and $R^2$ are independently selected from hydrogen, straight-chain and branched alkyl group having up to 10 carbon atoms or —$(CH_2)_m$Ar where Ar is phenyl, naphthyl or thienyl, each optionally substituted by one or two substituents selected independently from $C_1$–$C_6$ alkyl, halogen, $C_1$–$C_6$ alkoxide and trifluoromethyl;
or $NR^1R^2$ is 1, 2, 3, 4-tetrahydroquinolin-1-yl or 1, 2, 3, 4-tetrahydroisoquinoline-2-yl;
m is 1–5;
n is 1 or 2;
Y is hydrogen, $C_1$–$C_6$ alkyl, and $C_1$–$C_6$ alkoxy;
and the pharmaceutically acceptable salts thereof.

Pharmaceutically acceptable salts are prepared by methods well known to the art and are formed with both inorganic or organic acids including but not limited to fumaric, maleic, benzoic, ascorbic, pamoic, succinic, bismethylenesalicylic, methanesulfonic, ethanedisulfonic, acetic, oxalic, propionic, tartaric, salicyclic, citric, gluconic, lactic, malic, mandelic, cinnamic, citraconic, aspartic, stearic, palmitic, itaconic, glycolic, p-aminobenzoic, glutamic, benzene-sulfonic, hydrochloric hydrobromic, sulfuric, cyclohexylsulfamic, phosphoric and nitric acids.

DETAILED DESCRIPTION OF THE INVENTION

The compounds of Formula I can be prepared by the overall sequence as follows:

Scheme I

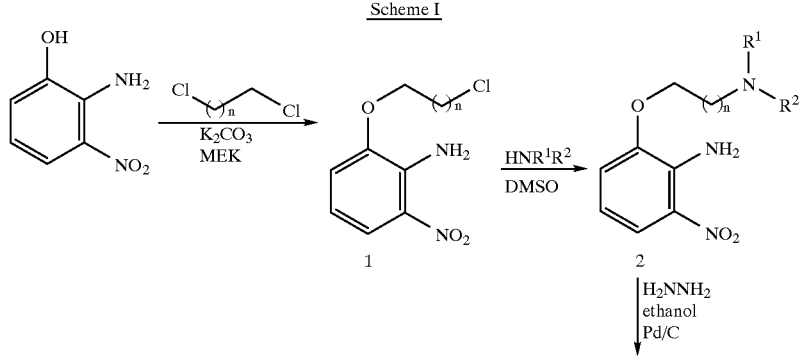

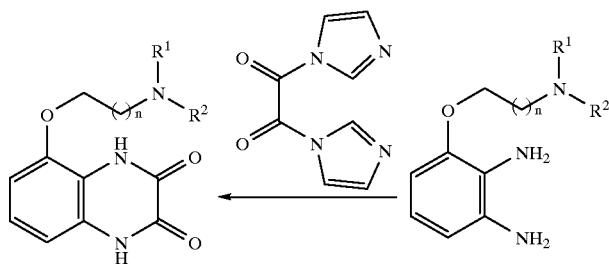

Where R¹ is hydrogen, invention compounds are prepared according to scheme II from intermediate 2 above wherein R¹ is hydrogen.

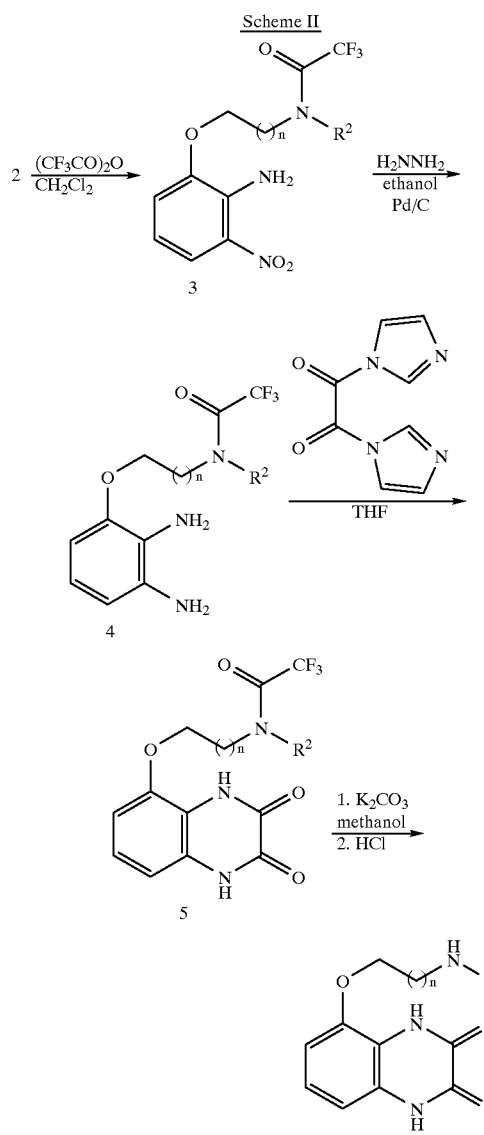

The compounds of Formula I, where R¹ and R² form a ring, are prepared by the overall sequence as follows:

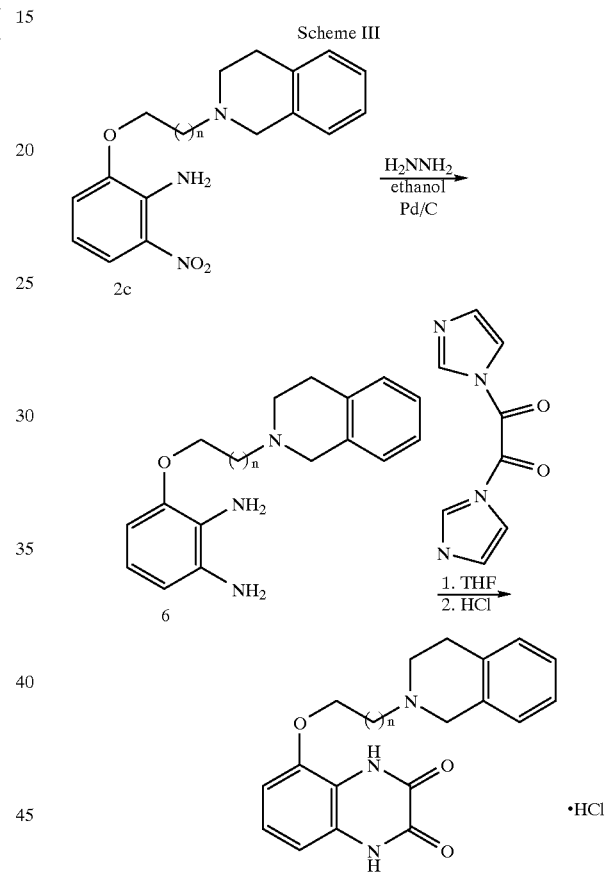

Specfic exemplification of the production of representative compounds of this invention is given in the following procedures. These syntheses are preformed using reagents and intermediates that are either commercially available or prepared according to standard literature procedures. These examples are included to illustrated the methods of this invention and are not to be construed as limiting in any way to this disclosure.

INTERMEDIATE 1

2-(2-Chloro-ethoxy)-6-nitro-phenylamine

A slurry containing 2-amino-3-nitrophenol (32.0 g, 0.208 mol), 1,2-dichloroethane (260.0 g, 2.65 mol), potassium carbonate (35.0 g, 0.252 mol) and 2-butanone (750 mL) was refluxed for 24 hr. The mixture was cooled, filtered and the solids were washed with ethyl acetate. The filtrate was concentrated to an oily residue that was dissolved in ethyl acetate (500 mL). The organic layer was washed with 1 N sodium hydroxide (250 mL), water (500 mL), and brine (2×500 mL), dried over anhydrous magnesium sulfate. Concentration of the filtered solution and trtuation of the residue with hexane afforded 37.8 g (84.6%) of product as an orange solid, mp 71–73° C.; MS (+)PBEI m/e 216/218 (M$^+$).

Elemental analysis for $C_8H_9ClN_2O_3$: Calc'd: C, 44.36; H, 4.19; N, 12.93; Found: C, 44.45; H, 4.02; N, 12.97

INTERMEDIATE 2a (2-(2-Benzylamino-ethoxy)-6-nitro-phenyl)-amine

A mixture of 2-(2-chloroethoxy)-6-nitrophenylamine (3.0 g, 13.8 mmol) and benzylamine (9.0 g, 84.0 mmol) was heated at 100–110° C. for 6 hr. The excess benzylamine was removed by distillation under vacuum (70–75° C./0.1 mm). The residue was poured into 1 N sodium hydroxide (300 mL) and extracted with ethyl acetate (2×300 mL). The combined organic layer was washed with water (2×300 mL) and brine (300 mL). The ethyl acetate layer was dried over anhydrous magnesium sulfate, filtered, and the solvent removed under vacuum to give 5.1 g of crude red oil. Purification by chromatography (500 g silica gel, ethyl acetate: 2 M $NH_3$ in methanol, 20:1) afforded 3.54 g (89.3%) of a red semi-solid, mp 33–60° C.; MS EI m/e 287 (M$^+$).

Elemental analysis for $C_{15}H_{17}N_3O_3$: Calc'd: C, 62.71; H, 5.96; N, 14.62; Found: C, 62.64; H, 6.04; N, 14.23

Following this general procedure utilizing 4-chlorobenzylamine and 1,2,3,4-tetrahydro-isoquinoline afforded respectively:

2b 2-[2-(4-Chloro-benzylamino)-ethoxy]-6-nitro-phenylamino quarter hydrate as an orange solid (87.8%): mp 61–62° C.; MS (+)CI m/e 322/324 (M+H)$^+$.

Elemental analysis for $C_{16}H_{19}N_3O_3 \cdot 0.25 H_2O$: Calc'd: C, 55.22; H, 5.10; N, 12.88; Found: C, 55.27; H, 4.96; N, 12.88
2c 2-[2-(3,4-Dihydro-1H-isoquinolin-2-yl)-ethoxy]-6-nitro-phenylamino as a yellow solid (87.1%), mp 95–96° C.; MS EI m/e 313 (M$^+$).

Elemental analysis for $C_{17}H_{19}N_3O_3$: Calc'd: C, 65.16; H, 6.11; N, 13.41; Found: C, 64.87; H, 6.11; N, 13.40

INTERMEDIATE 3a

N-[2-(2-Amino-3-nitro-phenyoxy)-ethyl]-N-benzyl-2,2,2-trifluoro-acetamide

To a solution containing 2-(2-benzylamino-ethoxy)-6-nitro-phenylamino (3a, 0.50 g, 1.74 mmol), triethylamine (0.50 mL) and methylene chloride (10 mL) was slowly added trifluoroacetic acid anhydride (0.32 mL, 2.26 mmol). After 2 hr, the reaction mixture was poured into 1 N sodium hydroxide (50 mL) and extracted with methylene chloride. The organic layer was washed with water (2×50 mL) and brine (50 mL), dried over anhydrous magnesium sulfate, filtered, and the solvent removed under vacuum to give a crude yellow residue. Crystallization of this material from ethyl acetate-hexane afforded 0.55 g (81.7%) of a yellow solid, mp 134–135° C.; MS EI m/e 383 (M$^+$).

Elemental analysis for $C_{17}H_{16}F_3N_3O_4$: Calc'd: C, 53.27; H, 4.21; N, 10.96; Found: C, 53.09; H, 4.35; N, 10.93

Following this general procedure and utilizing 2-[2-(4-chloro-benzylamino)ethoxy]-6-nitro-phenylamino afforded:
3b N-[2-(2-Amino-3-nitro-phenoxy)-ethyl]-N-(4-chlorobenzyl)-2,2,2-trifluoro-acetamide as a yellow solid (84.0%), mp 138–139° C.; MS (+)FAB m/e 418/420 (M+H)$^+$.

Elemental analysis for $C_{17}H_{15}ClF_3N_3O_4$: Calc'd: C, 48.88; H, 3.62; N, 10.06; Found: C, 48.66; H, 3.47; N, 9.82

INTERMEDIATE 4a

N-Benzyl-N-[2-(2,3-diamino-phenoxy)-ethyl]-2,2,2-trifluoro-acetamide

To a mixture containing N-[2-(2-amino-3-nitro-phenyoxy)-ethyl]-N-benzyl-2,2,2-trifluoro-acetamide (3a, 0.4 g, 1.04 mmol), 10% palladium on carbon (0.1 g) in ethanol (30 mL) was slowly added a solution of hydrazine hydrate (0.6 mL) in ethanol (10.0 mL). The mixture was heated to 55–60° C. and stirred at that temperature for 1 hr. The mixture was cooled to 25° C., filtered and the catalyst was washed with ethanol. The filtrate was concentrated under vacuum and the residue was diluted with ethyl acetate (100 mL). The organic layer was washed with water (2×100 mL) and brine (100 mL), dried over anhydrous magnesium sulfate, filtered, and the solvent removed under vacuum to give 0.32 g (87.5% crude yield) of product as a brown viscous oil; MS (+)FAB m/e 354 (M+H)$^+$.

Following this general procedure and utilizing N-[2-(2-amino-3-nitro-phenoxy)-ethyl]-N-(4-chloro-benzyl)-2,2,2-trifluoro-acetamide afforded:
4b N-(4-Chloro-benzyl)-N-[2-(2,3-diamino-phenoxy)-ethyl]-2,2,2-trifluoro-acetamide as a brown oil (80.9%); MS EI m/e 387/389 (M$^+$).

Elemental analysis for $C_{17}H_{17}ClF_3N_3O_2$: Calc'd: C, 52.65; H, 4.42; N, 10.84; Found: C, 52.47; H, 4.51; N, 10.60

INTERMEDIATE 5a

N-Benzyl-N-[2-(2,3-dioxo-1,2,3,4-tetrahydro-quinoxalin-5-yloxy)-ethyl]-2,2,2-trifluoro-acetamide A mixture of N-benzyl-N-[2-(2,3-diamino-phenoxy)-ethyl]-2,2,2-trifluoro-acetamide (0.49 g, 1.40 mmol) and oxalyl diimidazole (0.44 g, 2.09 mmol) in anhydrous tetrahydrofuran (20 mL) was refluxed for 2 hr. The reaction was poured into water and extracted with ethyl acetate (2×150 mL). The organic layer was dried over anhydrous magnesium sulfate, filtered, and the solvent removed under vacuum. Purification by chromatography (70 g silica gel, ethyl acetate) afforded 0.25 g (43.8%) of solid. Crystallization from ethyl acetatehexane gave a white solid, mp 218–220° C. MS EI m/e 407 (M$^+$).

Elemental analysis for $C_{19}H_{16}F_3N_3O_4$: Calc'd: C, 55.77; H, 3.90; N, 10.05; Found: C, 56.02; H, 3.96; N, 10.32

Following this general procedure and utilizing N-(4-chloro-benzyl)-N-[2-(2,3-diamino phenoxy)-ethyl]-2,2,2-trifluoro-acetamide, N-(4-chloro-benzyl)-N-[2-(2,3-dioxo-1,2,3,4-tetrahydroquinoxalin-5-yloxy)-ethyl]-2,2,2-trifluoro-acetamide (5b) was obtained a semi-solid material (47%).

INTERMEDIATE 6

3-[2-(3,4-Dihydro-1H-isoquinolin-2-yl)-ethoxy]-benzene-1,2-diamine

The general procedure followed in intermediate 4 using 2-[2-(3,4-dihydro-1H-isoquinolin-2-yl)-ethoxy]-6-nitro-phenylamine (2c) afforded 3-[2-(3,4-dihydro-1H-isoquinolin-2-yl)-ethoxy]-benzene-1,2-diamine as a solid (95%), mp 76–77° C. This material was characterized as the dihydrochloride 0.4 $H_2O$ salt; MS EI m/e 283 (M$^+$).

Elemental analysis for $C_{17}H_{21}N_3O \cdot 2 HCl \cdot 0.4 H_2O$: Calc'd: C, 56.17; H, 6.60; N, 11.56; Found: C, 56.15; H, 6.68; N, 11.25

EXAMPLE 1

5-(2-Benzylamino-ethoxy)-1,4-dihydro-quinoxaline-2,3-dione

A suspension of potassium carbonate (0.33 g, 2.40 mmol) and N-benzyl-N-[2-(2,3-dioxo-1,2,3,4-tetrahydroquinoxalin-5-yloxy)-ethyl]-2,2,2-trifluoro-acetamide (0.21g, 0.52 mmol) in methanol-water (25 mL:1.5 mL) was heated to reflux for 2 hr. The solvent was evaporated and the residue dissolved in ethyl acetate (100 mL). The organic layer was washed with water (80 mL), dried over anhydrous magnesium sulfate, filtered, and the solvent concentrated under vacuum to give the crude base as a white solid, mp 242–245° C. Without further purification, this material was dissolved in methanol and treated with an excess amount of 1 N HCl in ether to afford 0.11 g (75.0%) of the hydrochloride salt as a white solid, mp >250° C.: MS (+)ESI m/e 312 (M+H$^+$).

Elemental analysis for $C_{16}H_{17}N_3O_2$.HCl: Calc'd: C, 60.09; H, 5.67; N, 13.14; Found: C, 59.84; H, 5.59; N, 12.92

EXAMPLE 2

5-[2-(4-Chloro-benzylamino)-ethoxy]-1,4-dihydro-quinoxaline-2,3-dione

Following the general procedure used in example 1 using N-(4-chloro-benzyl)-N-[2-(2,3-dioxo-1,2,3,4-tetrahydro-quinoxalin-5-yloxy)-ethyl]-2,2,2-trifluoro-acetamide afforded 5-[2-(4-chloro-benzylamino)-ethoxy]-1,4-dihydro-quinoxaline-2,3-dione.HCl.0.75 H$_2$O as a beige solid (90.0%), mp >250° C.; MS (+)FAB m/e 346 (M+H$^+$).

Elemental analysis for $C_{17}H_{16}ClN_3O_3$: Calc'd: C, 60.09; H, 5.67; N, 13.14; Found: C, 59.84; H, 5.59; N, 12.92

EXAMPLE 3

5-[2-(3,4-Dihydro-1H-isoquinolin-2-yl)-ethoxy]-1,4-dihydro-quinoxaline-2,3-dione The general procedure used in example 1 using 2-[2-(3,4-dihydro-1H-isoquinolin-2-yl)ethoxy]-6-nitro-phenylamine afforded 5-[2-(3,4-dihydro-1H-isoquinolin-2-yl)-ethoxy]-1,4-dihydro-quinoxaline-2,3-dione.quarter hydrate as a white solid (66.7%), mp >250° C.; MS (+)FAB m/e 338 (M+H$^+$).

Elemental analysis for $C_{19}H_{19}N_3O_3$.0.25 H$_2$O: Calc'd: C, 66.75; H, 5.75; N, 12.29; Found: C, 66.93; H, 5.60; N, 12.25

Treatment of the above solid with excess 1N hydrogen chloride in ether gave the monohydrate hydrochloride salt of the tide compound as a white solid (90.0%), mp 243–245° C.; MS (+)FAB m/e 338 (M+H$^+$).

Elemental analysis for $C_{19}H_{19}N_3O_3$.HCl.H$_2$O: Calc'd: C, 58.24; H, 5.66; N, 10.72; Found: C, 58.20; H, 5.43; N, 10.85

The compounds of this invention are dopamine autoreceptor agonists, that is, they serve to modulate the synthesis and release of the neurotransmitter dopamine. They are thus useful for treatment of disorders of the dopaminergic system, such as schizophrenia, Parkinson's disease and Tourette's syndrome. Such agents are partial agonists at the postsynaptic dopamine D$_2$ receptor and are thereby useful in the treatment of alcohol and drug addiction.

Affinity for the dopamine autoreceptor was established by a modification of the standard experimental test procedure of Seamen and Schaus, *European Journal of Pharmacology* 203, 105–109, 1991, wherein homogenized rat striatal brain tissue is incubated with $^3$H-quinpirole (Quin.) and various concentrations of test compound, filtered and washed and counted in a Betaplate scintillation counter.

High affinity for the dopamine D-2 receptor was established by the standard experimental test procedure of Fields, et al., *Brain Res.*, 136, 578 (1977) and Yamamura et al., eds., *Neurotranrutter Receptor Binding*, Raven Press, N.Y. (1978) wherein homogenized limbic brain tissue is incubated with $^3$H-spiroperidol (Spiper.) and various concentrations of test compound, filtered and washed and shaken with Hydrofluor scintillation cocktail (National Diagnostics) and counted in a Packard 460 CD scintillation counter.

The results of the tests with compounds representative of this invention are given in the immediately following table.

| Example No. | IC$_{50}$ (nM) D$_2$ Quin. | IC$_{50}$ (nM) D$_2$ Spiper | Ratio |
|---|---|---|---|
| 1 | 20.8 | 2187 | 105.1 |
| 2 | 64.6 | | |
| 3 | | | |

Hence, the compounds of this invention effect the synthesis of the neurotransmitter dopamine and thus are useful in the treatment of dopaminergic disorders such as schizophrenia, Parkinson's disease, Tourette's Syndrome, alcohol addiction, cocaine addiction, and addiction to analagous drugs.

Applicable solid carriers for pharmaceutical compositions containing the compounds of this invention can include one or more substances which may also act as flavoring agents, lubricants, solubilizers, suspending agents, fillers, glidants, compression aids, binders or tablet-disintergrating agents or an encapsulating material. In powders, the carrier is a finely divided solid which is in admixture with the finely divided active ingredient. In tablets, the active ingredient is mixed with a carrier having the necessary compression properties in suitable proportions and compacted in the shape and size desired. The powders and tablets preferably contain up to 99% of the active ingredient. Suitable solid carriers include, for example, calcium phosphate, magnesium stearate, talc, sugars, lactose, dextrin, starch, gelatin, cellulose, methyl cellulose, sodium carboxymethyl cellulose, polyvinylpyrrolidine, low melting waxes and ion exchange resins.

Liquid carriers may be used in preparing solutions, suspensions, emulsions, syrups and elixirs. The active ingredient of this invention can be dissolved or suspended in a pharmaceutically acceptable liquid carrier such as water, an organic solvent, a mixture of both or pharmaceutically acceptable oils or fat. The liquid carrier can contain other suitable pharmaceutical additives such as solubilizers, emulsifiers, buffers, preservatives, sweeteners, flavoring agents, suspending agents, thickening agents, colors, viscosity regulators, stabilizers or osmo-regulators. Suitable examples of liquid carriers for or/and parenteral administration include water (particularly containing additives as above e.g. cellulose derivatives, preferably sodium carboxymethyl cellulose solution), alcohols (including monohydric alcohols and polyhydric alcohols e.g. glycols) and their derivatives, and oils (e.g. fractionated coconut oil and arachis oil). For parenteral administration the carrier can also be an oily ester such as ethyl oleate and isopropyl myristate. Sterile liquid carriers are used in sterile liquid form compositions for parenteral administration.

Liquid pharmaceutical compositions which are sterile solutions or suspensions can be utilized by, for example, intramuscular, intraperitoneal or subcutaneous injection. Sterile solutions can also be administered intravenously. Oral administration may be either liquid or solid composition form.

Preferably the pharmaceutical composition is in unit dosage form, e.g. as tablets or capsules. In such form, the composition is subdivided in unit dose containing appropriate quantities of the active ingredient; the unit dosage forms can be packaged compositions, for example packeted powders, vials, ampoules, prefilled syringes or sachets containing liquids. The unit dosage form can be, for example, a capsule or tablet itself, or it can be the appropriate number of any such compositions in package form.

The dosage to be used in the treatment of a specific psychosis must be subjectively determined by the attending physician. The variables involved include the specific psychosis and the size, age and response pattern of the patient.

What is claimed is:

1. A compound of the Formula I:

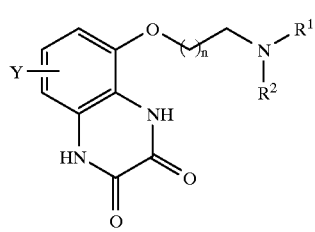

wherein:
 $R^1$ and $R^2$ are independently selected from hydrogen, straight-chain and branched alkyl group having up to 10 carbon atoms or —$(CH_2)_m$Ar where Ar is phenyl, naphthyl or thienyl, each optionally substituted by one or two substituents selected independently from $C_1$–$C_6$ alkyl, halogen, $C_1$–$C_6$ alkoxide and trifluoromethyl;
 or $NR^1R^2$ is 1, 2, 3, 4-tetrahydroquinolin-1-yl or 1, 2, 3, 4-tetrahydroisoquinolin-2-yl;
 m is 1–5;
 n is 1 or 2;
 Y is hydrogen, $C_1$–$C_6$ alkyl, and $C_1$–$C_6$ alkoxy;
 or a pharmaceutically acceptable salt thereof.

2. A compound according to claim 1 which is 5-(2-Benzylamino-ethoxy)-1,4-dihydro-quinoxaline-2,3-dione.

3. A compound according to claim 1 which is 5-[2-(4-Chloro-benzylamino)-ethoxy]-1,4-dihydro-quinoxaline-2,3-dione.

4. A compound according to claim 1 which is 5-[2-(3,4-Dihydro-1H-isoquinolin-2-yl)-ethoxy]-1,4-dihydro-quinoxaline-2,3-dione.

5. A method of treating schizophrenia or Parkinson's Disease which comprises administration to a mammal in need of such treatment of an effective amount of a compound of Formula I

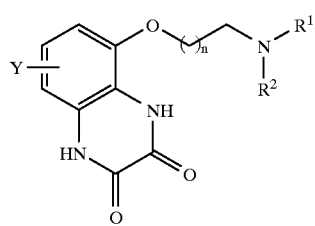

wherein:
 $R^1$ and $R^2$ are independently selected from hydrogen, straight-chain and branched alkyl group having up to 10 carbon atoms or —$(CH_2)_m$Ar where Ar is phenyl, naphthyl or thienyl, each optionally substituted by one or two substituents selected independently from $C_1$–$C_6$ alkyl, halogen, $C_1$–$C_6$ alkoxide and trifluoromethyl;
 or $NR^1R^2$ is 1, 2, 3, 4-tetrahydroquinolin-1-yl or 1, 2, 3, 4-tetrahydroisoquinolin-2-yl;
 m is 1–5;
 n is 1 or 2;
 $R^1$ is hydrogen or $C_1$–$C_6$ alkyl;
 Y is hydrogen, $C_1$–$C_6$ alkyl, and $C_1$–$C_6$ alkoxy;
 or a pharmaceutically acceptable salt thereof.

6. The method according to claim 5 wherein the compound of Formula I is selected from 5-(2-Benzylamino-ethoxy)-1,4-dihydro-quinoxaline-2,3-dione, 5-[2-(4-Chloro-benzylamino)-ethoxy]-1,4-dihydro-quinoxaline-2,3-dione, and 5-[2-(3,4-Dihydro-1H-isoquinolin-2-yl)-ethoxy]-1,4-dihydro-quinoxaline-2,3-dione.

7. A pharmaceutical composition comprising a pharmaceutically acceptable carrier and a therapeutically effective amount of a compound of Formula I

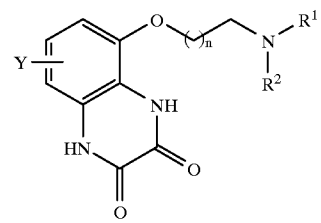

wherein:
 $R^1$ and $R^2$ are independently selected from hydrogen, straight-chain and branched alkyl group having up to 10 carbon atoms or —$(CH_2)_m$Ar where Ar is phenyl, naphthyl or thienyl, each optionally substituted by one or two substituents selected independently from $C_1$–$C_6$ alkyl, halogen, $C_1$–$C_6$ alkoxide and trifluoromethyl;
 or $NR^1R^2$ is 1, 2, 3, 4-tetrahydroquinolin-1-yl or 1, 2, 3, 4-tetrahydroisoquinolin-2-yl;
 m is 1–5;
 n is 1 or 2;
 Y is hydrogen, $C_1$–$C_6$ alkyl, and $C_1$–$C_6$ alkoxy;
 or a pharmaceutically acceptable salt thereof.

* * * * *